United States Patent
Peters et al.

(10) Patent No.: US 11,738,347 B2
(45) Date of Patent: Aug. 29, 2023

(54) LIQUID HANDLING SYSTEM AND METHOD

(71) Applicant: Innatoss Laboratories B.V., Oss (NL)

(72) Inventors: Wolfram Julius Paul Peters, Amsterdam (NL); Michiel De Haan, Haarlem (NL); Cornelia Maria De Jong, Diemen (NL); Freerk Van Oudheusden, Voorhout (NL); Ingmar Christiaan Maurice, Amsterdam (NL); Marlies Van Dullemen, Leiden (NL); Antonius Franciscus Cornelia Maria Smetsers, Nijmegen (NL); Anja Garritsen, Oss (NL)

(73) Assignee: INNATOSS LABORATORIES B.V., Ab Oss (NL)

( * ) Notice: Subject to any disclaimer, the term of this patent is extended or adjusted under 35 U.S.C. 154(b) by 306 days.

(21) Appl. No.: 16/641,108

(22) PCT Filed: Aug. 24, 2018

(86) PCT No.: PCT/EP2018/072917
§ 371 (c)(1),
(2) Date: Feb. 21, 2020

(87) PCT Pub. No.: WO2019/038437
PCT Pub. Date: Feb. 28, 2019

(65) Prior Publication Data
US 2020/0206745 A1    Jul. 2, 2020

(30) Foreign Application Priority Data

Aug. 24, 2017   (EP) .................................. 17187807

(51) Int. Cl.
*B01L 3/00*    (2006.01)
*A61B 5/15*    (2006.01)
*G01N 35/10*   (2006.01)

(52) U.S. Cl.
CPC ........ *B01L 3/563* (2013.01); *A61B 5/150251* (2013.01); *G01N 35/1065* (2013.01);
(Continued)

(58) Field of Classification Search
CPC ............... A61B 5/150251; B01L 3/563; B01L 2200/0684; B01L 2200/0861;
(Continued)

(56) References Cited

U.S. PATENT DOCUMENTS 3,494,351 A * 2/1970 Horn ................ A61B 5/150259
                                                    604/191
5,143,084 A    9/1992 Macemon et al.
(Continued)

FOREIGN PATENT DOCUMENTS

EP    396016 A2    11/1990
EP    486059 A1     5/1992
(Continued)

OTHER PUBLICATIONS

International Search Report dated Oct. 15, 2018, for corresponding International Patent Application No. PCT/EP2018/072917, filed Aug. 24, 2018.
(Continued)

*Primary Examiner* — Jill A Warden
*Assistant Examiner* — Dwayne K Handy
(74) *Attorney, Agent, or Firm* — Steven M. Koehler; Westman, Champlin & Koehler, P.A.

(57) ABSTRACT

A liquid handling system and method, e.g., for testing blood samples. The system comprises a cartridge, and a transfer device couplable to a liquid reservoir. The cartridge comprises compartments with an inlet, closed by a seal, and an outlet, closed by a gas-permeable liquid-tight filter. Keying portions define a relative position and orientation of the cartridge and the transfer device. Penetrating elements of the
(Continued)

transfer device penetrate the seal of each compartment, the penetrating elements having lumina for fluidly connecting the reservoir and each compartment cavity of the cartridge.

20 Claims, 12 Drawing Sheets

(52) U.S. Cl.
CPC ..... *B01L 2200/025* (2013.01); *B01L 2200/04* (2013.01); *B01L 2200/0684* (2013.01); *B01L 2300/044* (2013.01); *B01L 2300/0672* (2013.01); *B01L 2300/0851* (2013.01); *B01L 2300/0861* (2013.01)

(58) Field of Classification Search
CPC ....... B01L 2300/044; B01L 2300/0672; B01L 2200/04; B01L 2300/0861; A61J 1/20; A61J 1/2003; A61J 1/2058
See application file for complete search history.

(56) References Cited

U.S. PATENT DOCUMENTS

| | | | |
|---|---|---|---|
| 5,145,565 A | | 9/1992 | Kater et al. |
| 5,329,976 A | * | 7/1994 | Haber ................... A61J 1/2096 604/407 |
| 5,505,721 A | | 4/1996 | Leach et al. |
| 6,021,824 A | | 2/2000 | Larsen et al. |
| 9,226,875 B2 | | 1/2016 | Foshee et al. |
| 9,386,948 B2 | | 7/2016 | Holmes et al. |
| 9,427,184 B2 | | 8/2016 | Holmes et al. |
| 9,623,175 B2 | | 4/2017 | Fini et al. |
| 9,662,621 B2 | | 5/2017 | Beyer et al. |
| 9,877,674 B2 | | 1/2018 | Holmes et al. |
| 9,908,113 B2 | | 3/2018 | Sloan et al. |
| 2004/0253143 A1 | | 12/2004 | Fukushima |
| 2012/0089088 A1 | | 4/2012 | Foshee et al. |
| 2013/0060226 A1 | | 3/2013 | Fini et al. |
| 2014/0073990 A1 | | 3/2014 | Holmes et al. |
| 2015/0029816 A1 | | 1/2015 | Beyer et al. |
| 2015/0231627 A1 | | 8/2015 | Sloan et al. |
| 2017/0021355 A1 | | 1/2017 | Olivier et al. |
| 2017/0042460 A1 | | 2/2017 | Holmes et al. |
| 2018/0214058 A1 | | 8/2018 | Holmes et al. |

FOREIGN PATENT DOCUMENTS

| | | |
|---|---|---|
| EP | 1614464 A1 | 1/2006 |
| WO | 2010141632 A2 | 12/2010 |
| WO | 2011141200 A1 | 11/2011 |
| WO | 2013132414 A1 | 9/2013 |
| WO | 2014039909 A1 | 3/2014 |
| WO | 2014088606 A2 | 6/2014 |
| WO | 2014145330 A2 | 9/2014 |
| WO | 2014145935 A1 | 9/2014 |
| WO | 2015134809 A1 | 9/2015 |
| WO | 2015138818 A1 | 9/2015 |

OTHER PUBLICATIONS

Written Opinion of the International Searching Authority dated Oct. 15, 2018, for corresponding International Patent Application No. PCT/EP2018/072917, filed Aug. 24, 2018.

European Office Action in corresponding European Patent Application No. 18759623.4 dated Feb. 18, 2021.

* cited by examiner

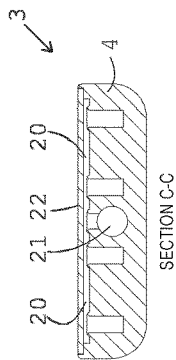
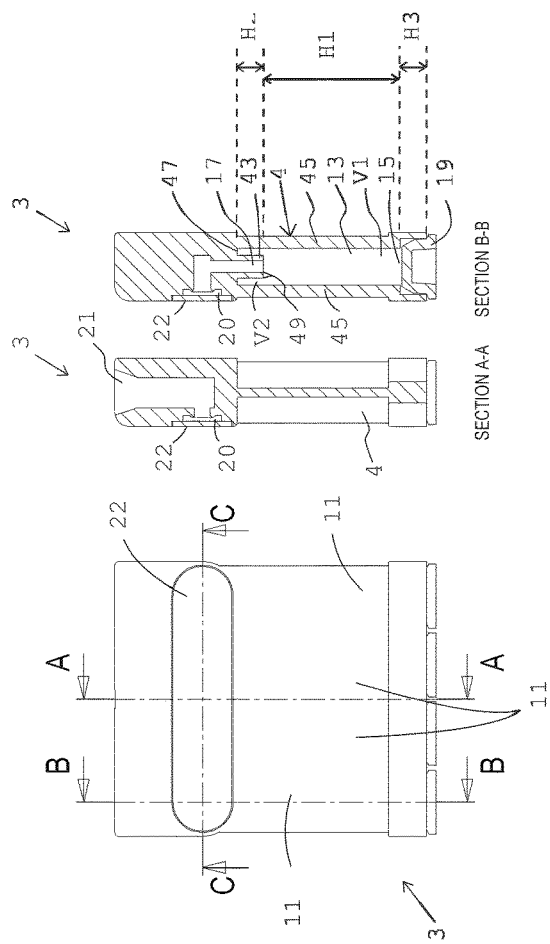
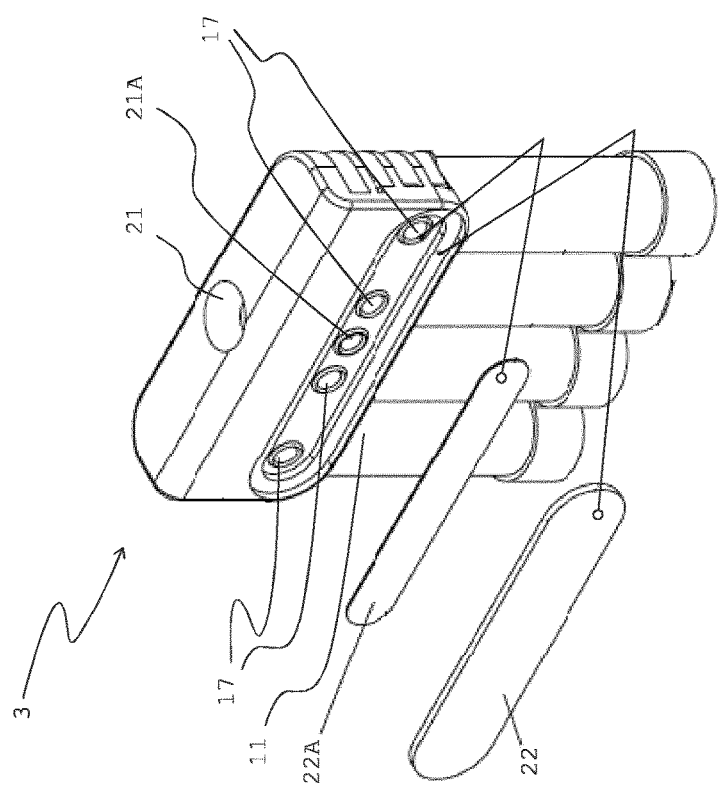

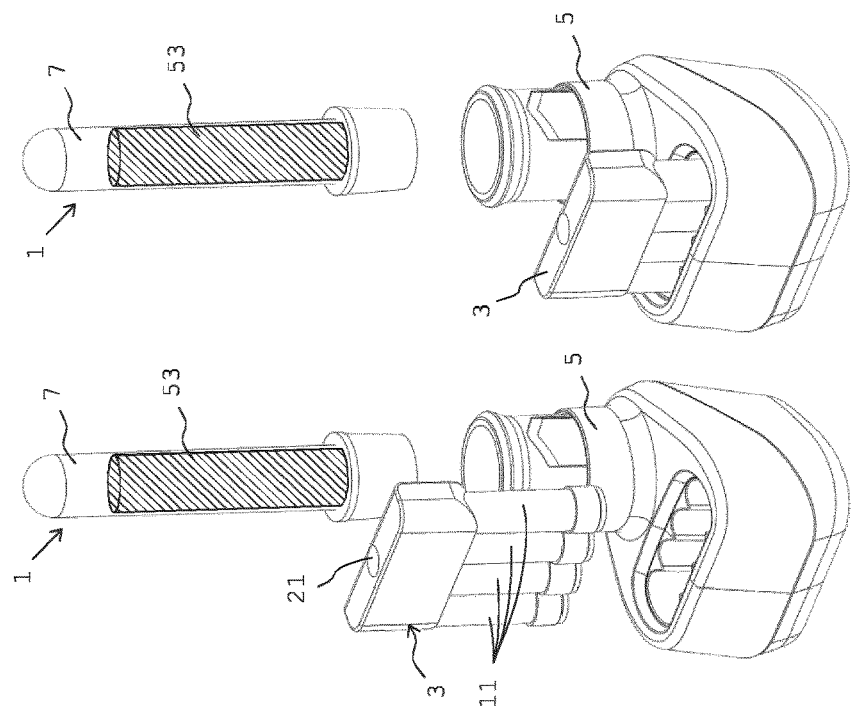
Fig.12
Fig.11
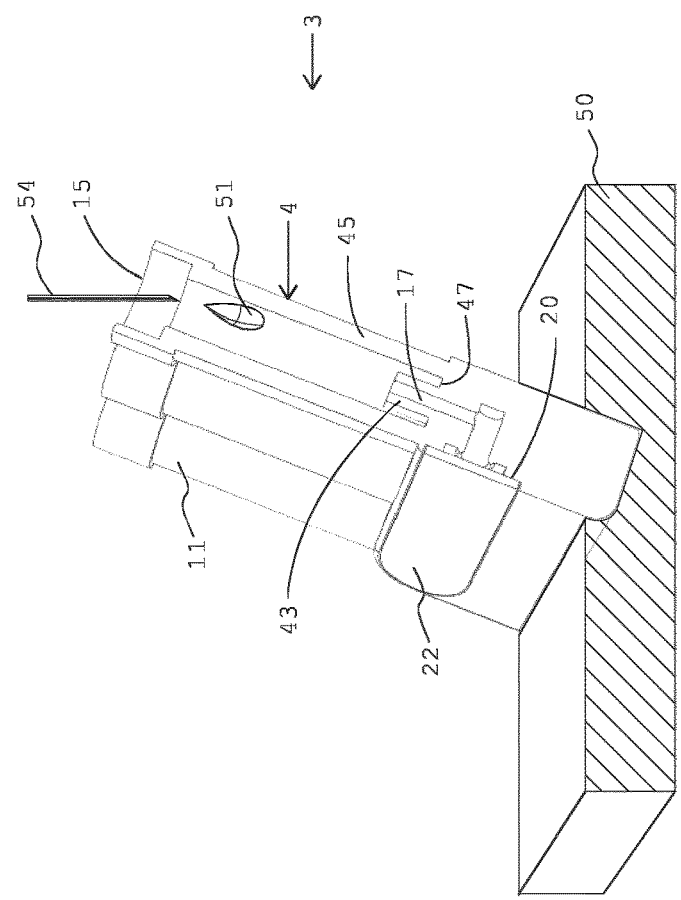
Fig.10

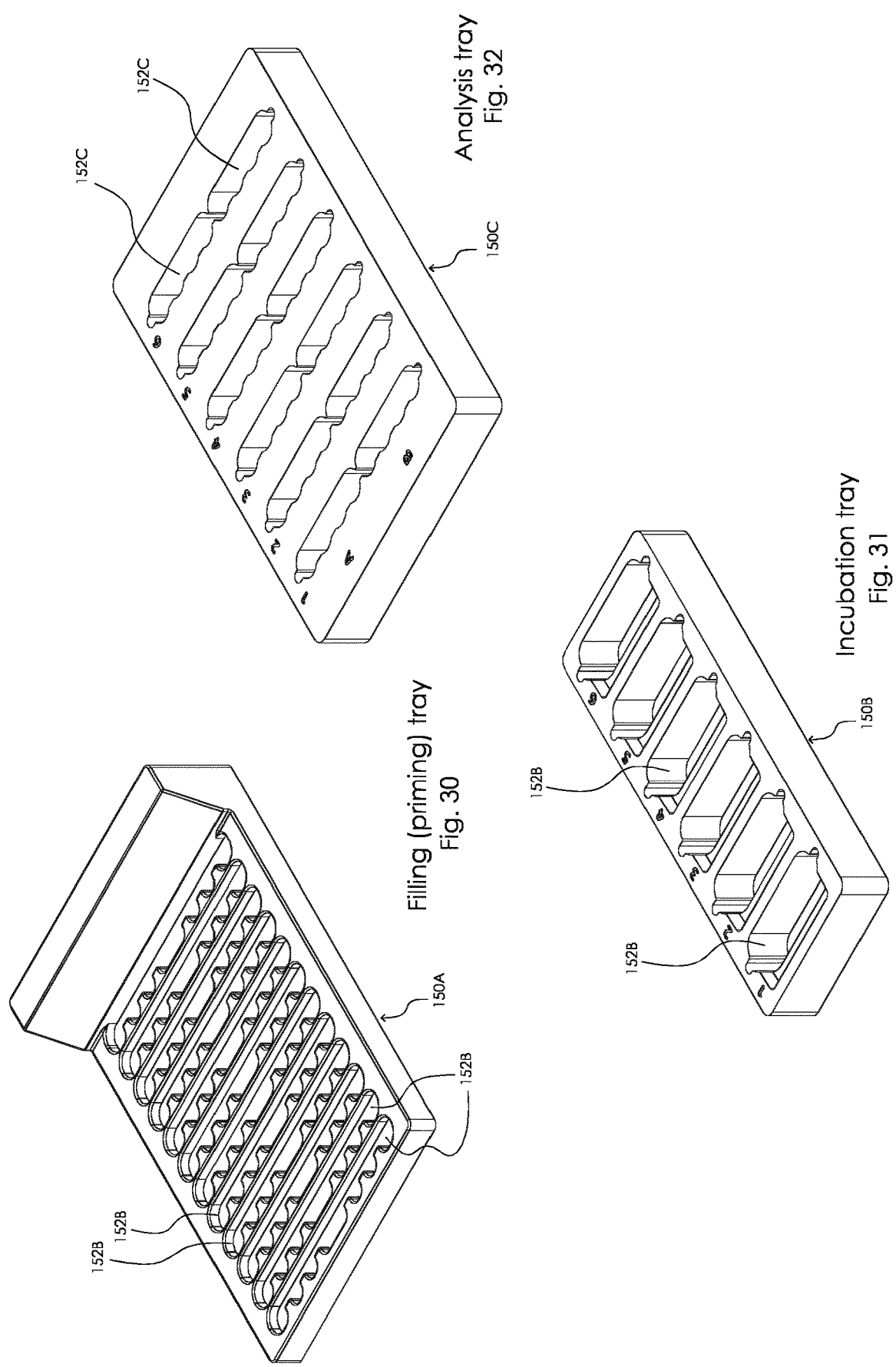

LIQUID HANDLING SYSTEM AND METHOD

CROSS-REFERENCE TO RELATED APPLICATION

The present application is a national stage of and claims priority of International patent application Serial No. PCT/EP2018/072917, filed Aug. 24, 2018, and published in English as WO 2019/038437.

TECHNICAL FIELD

The present disclosure relates to a method and a system for handling liquids, such as sampling, separating, testing and/or transportation of fluids, in particular biological fluids, more in particular bodily fluids, which may be mammalian e.g. human. Specifically, the present disclosure relates to comparative testing of bodily fluids.

BACKGROUND

Sampling and tests on fluid samples, in particular biological samples, e.g. on blood, may require interaction of the sample with various substances, e.g. blood interaction with one or more antigens, and/or a comparison between different portions of the sample subject to different (partial) tests. A test protocol may therefore require withdrawal of the fluid to be studied, (re-) distribution of the fluid over several containers into respective several amounts forming respective samples, causing development and/or interaction with a substance of at least one of the samples and determining a result of the development and/or interaction. In a particular example, the sample may be human blood and the development and interaction comprises interaction with various antigens over a period of time.

Several devices are known, in which plural amounts of bodily fluids, e.g. blood, are contained in individual volumes for transport and/or testing.

In relation with the above, a number of publications is noted disclosing at least one of collecting, transporting and testing blood: WO 2015/0138818, WO 2014/145330, WO 2015/134809, U.S. Pat. No. 9,427,184, WO 2014/039909, WO 2014/145935, WO 2014/088606, U.S. Pat. Nos. 9,386,948, 5,505,721, EP 486 059 and EP 396 016. Further, WO 2010/141632 discloses a system having an improved gate for the connection of vials, and WO 2011/141200 relates to a tubing set having an improved gate for the connection of vials for redistribution into vials and mixing of fluid samples between and in several vials.

For some tests the amount(s) of the fluid must be accurately determined; in such cases proper control of filling the volume or, respectively, the volumes is required. When dealing with biological samples, safety demands and precautions regarding contamination of the samples by external factors are a major concern. Conversely, protection of an operator against contamination or infection by, or due to, the sample and/or handling thereof are of great importance. Further, establishing and maintaining separation of different samples is important.

It has been considered that further improvements are desired for transporting and/or testing of bodily fluids requiring the above-referenced amount of control and/or contamination control in a practical setting, in particular involving temporal and/or temperature constraints in an uncontrolled environment (non-laboratory environment) and/or with operators having little experience with the test and associated devices.

SUMMARY

In view of the above, a system, a method and associated devices as indicated above, such as a cartridge, are herewith provided as set out below and in particular according to the appended claims.

Accordingly, a sample system is provided comprising a cartridge and a transfer device couplable to a liquid reservoir and having a normal operating configuration, e.g. being positionable on a horizontal surface. The cartridge comprises at least one compartment having a compartment cavity configured to contain an amount of liquid and having an inlet and an outlet to the compartment cavity, in particular the cartridge comprising plural juxtaposed separate compartments each having a compartment cavity configured to contain a respective amount of liquid and having an inlet and an outlet to the compartment cavity. Each inlet is a liquid inlet closed by a penetrable seal and each outlet being a gas outlet closed by a filter material allowing passage of a gas but blocking liquid passage. Suitable filter materials are known in the art, e.g. see the article Aerosol Filters, Journal of Aerosol medicine, D. Hochrainer, February 2009, 5(3), p. 201-207. The transfer device and the cartridge have matching keying portions defining a relative position and orientation of the cartridge and the transfer device when mated in a releasable manner. When mated and with the transfer device being in the normal operating configuration, each outlet is preferably positioned above the respective inlet. One or more penetrating elements of the transfer device are arranged for penetrating, or causing to be penetrated, the seals of each compartment when the keying portions are mated, when coupled, the reservoir and each compartment cavity of the cartridge through the one or more penetrating elements, e.g. the penetrating elements having lumina for said fluidly connecting.

The system allows filling the compartment cavity or—cavities by application of a pressure difference across the filter, e.g. suction filling and/or pressure-filling, wherein the liquid displaces air or another gas in the compartment which may escape through the filter. Also, capillary flow and/or passive flow (e.g., using one or more valves to avoid overflow and/or backflow) are possible. Application of a pressure difference facilitates operation with a reservoir that itself is provided with an internal pressure different from ambient pressure, e.g. an overpressure or an underpressure, which pressure difference may be associated with transferring the liquid from the reservoir; e.g. emptying the reservoir may cause development or increase of an underpressure.

Thus, a sample may be prepared in the cartridge from the reservoir or, respectively, plural samples may be prepared in respective compartments of the cartridge, starting from the reservoir. The seal reduces or prevents spilling and/or contamination of the liquid and/or of the compartment. The penetrating elements are hollow devices, e.g. a hollow needle, enabling transfer of the liquid through them. In a case of plural compartments, the transfer device functions as a manifold from the reservoir to the compartments.

The seal may be provided by an elastic material and/or it may be a capillary seal. For a capillary seal the inlet has an opening and the size and/or material properties of at least part of the inlet at or near the opening in combination with the surface tension and/or adhesion properties of the liquid (predominantly: opening shape and adhesion force for the fluid) prevent liquid transfer therethrough, absent significant pressure difference to penetrate the seal and force the fluid through the opening.

The seal being elastic and/or a capillary seal, enables that the seal closes again upon decoupling the cartridge and the transfer device. The seal may be at least part of a cap, the cap possibly being resilient as a whole. Also, other types of seal and combinations may be provided.

The penetration may be by physically penetrating a penetrable seal like an elastic seal. Another option, independently or in combination, is to cause a liquid penetrating an element of the seal e.g. a septum or membrane, which may be elastic. The liquid may be in the form of a liquid jet.

The orientation determination of the cartridge due to the coupling between the transfer device and the cartridge, and the outlet being closed by the filter, enables filling each compartment to a level determined by the respective filter; when the liquid level reaches the filter further filling of the compartment is prevented. Thus, the amount of liquid to be filled into each compartment may be accurately determined and/or designed. This holds for a cartridge having a single compartment as well as for cartridges having plural compartments. Note that the transfer device may also comprise plural keying portions for simultaneously or sequentially coupling to plural cartridges and fluidly connecting, when coupled, the reservoir and each compartment cavity of each cartridge through the one or more penetrating elements. The mated keying portions of the transfer device and the cartridge assist correct pairing of parts and/or correct placement of the parts together, reducing mistakes.

The orientation of the cartridge when coupled with the transfer device may require inverting the cartridge relative to an operating orientation in preceding and/or subsequent stages of use of the cartridge, wherein the inlet may be positioned at the same height or above the outlet.

The coupling of the cartridge with the transfer device may provide, apart from the fluid communication through the penetrating elements, a substantially liquid-tight and preferably also gas-tight connection between the cartridge and the transfer device.

Note that in the present disclosure, unless otherwise specified, the word "orientation" and directions like "above" and "below" generally refer to the orientation of an object under consideration relative to the surroundings, in particular relative to earth's gravity pointing down, as customary. Further, words like "detachable", "reversibly couplable" "removably connected" and similar are intended to mean that respective parts may be disconnected essentially without destruction of either part, e.g. excluding structures in which the parts are integral (e.g. welded or moulded as one piece), but including structures in which parts are attached by, and/or being formed as, mated connectors, decouplable fasteners, releasable self-fastening features, etc.

One or more of the compartments, possibly the cartridge as a whole, may extend along an axis, e.g. having a cylindrical and/or conical shape. The inlet and the outlet may be substantially opposite each other generally along the axis, filling the compartment may then generally proceed along the axis. The outlet of at least one of the compartments may have an opening to the compartment that may be oriented perpendicular to the axis. This facilitates that the liquid level contacts the outlet more or less abruptly which may provide a clear signal of complete filling of the compartment to that level.

The system may comprise plural compartments, preferably the cartridge comprising plural compartments. The outlets of each compartment may be fluidly connected forming a manifold from each of the outlets of the compartments to an exit, e.g., a single exit. Preferably the exit is provided with a connector for connection to a suction device. The suction device may be a syringe, a pipette-pump, a connection to a hospital vacuum line or any other suitable apparatus or vacuum source, etc.

The manifold facilitates maintenance and operation of the system since only a single exit need be considered. This may facilitate construction, maintenance and/or hygiene. Also, a suction source may be connected to the exit, e.g. with a suitable connector, for simultaneously drawing liquid into the compartments from the reservoir.

The cartridge may be formed as an assembly, wherein at least part of the manifold may be detachable from one or more of the compartments. The manifold may serve to keep plural components together. Also, or alternatively, plural compartments may be attached together and/or be formed as an integral, or even unitary, object.

The filling level of each compartment is determined by the respective filter, thus rendering possible filling speed differences irrelevant.

When the cartridge and the transfer device are coupled together by the mated keying portions, the outlet of at least one of the compartments may have an opening to the compartment offset from a top wall of the compartment, such that the compartment cavity comprises a first volume portion below the opening and a second volume portion above the opening. E.g. the gas exit may protrude into the compartment cavity.

This facilitates providing an airspace in the compartment. An airspace facilitates opening of the compartment without spilling contents thereof. Further, a well-defined gas volume may be relevant for one or more reactions of the sample. Further, the second volume may accommodate a reactant dose, e.g. a bioreactant such as an antibody dose, without affecting the amount of liquid (to be) contained in the first volume portion, or the other way around.

At least one of the compartments may contain a reactant dose to interact with at least a portion of the liquid. The reactant may be a chemical substance, a binding moiety, like an antibody, an antigen, a combination thereof, or any other composition with which at least part of the sample is to interact in a predetermined manner, e.g. showing a chemical reaction and/or a biological effect sufficient to produce a detectable and measurable and/or quantifiable effect. Such effect may be an increase or decrease of a component of the sample and/or of a component of the reactant. Preferably a compartment is provided with a reactant dose prior to introduction of the liquid from the reservoir and the transfer device.

Such reactant dose may be located either in the first volume or in the second volume, which may be exclusively such that the reactant dose is not located in both volumes. Thus, the volume of the reactant dose in one of the first and second volumes may not interfere with the volume of liquid in, or (to be) filled into, the other one of the first and second volumes. Thus, an accurate amount of the liquid may be filled into the first volume of the compartment cavity. Interaction of the liquid with reactant dose in the second volume may, e.g., be initiated by shaking and/or modifying the orientation of the compartment such as decoupling the cartridge from the transfer device and/or inverting the cartridge.

One or more compartments may comprise, preferably adjacent its outlet, a rupturing tip for rupturing liquid bubbles formed in a liquid inside the compartment. Bubble formation may in particular occur with liquid transfer wherein the liquid is forced into the compartment cavity by a pressure difference. E.g., mammalian blood drawn into the compartment cavity may form bubbles which can be removed by the rupturing tip. Removal of bubbles facilitates proper definition of a liquid level in the compartment and it may prevent accidental wetting of the filter and/or otherwise obstructing gas flow through the outlet which could hinder filling of the compartment.

Preferably, in a cartridge comprising plural compartments, at least some of the compartment cavities have identical volumes and/or the outlets of the compartments are positioned at equal heights when the cartridge and the transfer device are coupled and in the normal operating configuration.

A relatively narrow and/or short outlet channel between the compartment cavity and the filter may form a relatively small volume fraction of the volume of the compartment cavity associated with the respective outlet.

When the volumes and in particular when the (intended) maximum filling levels of each compartment, associated with its outlet and/or the filter, are equal, this facilitates checking proper operation and use of the system. Preferably at least part of the cartridge is at least translucent or even transparent, facilitating optical checking. Similarly, at least part of the transfer device may be at least translucent or even transparent.

The transfer device and the reservoir may have mated keying portions defining a relative position and orientation of the reservoir and the transfer device when coupled together by the mated keying portions. This facilitates proper use of the system, assisting personnel with little training and/or experience with the system.

One or more penetrating elements of the transfer device may be configured to penetrate, and/or to cause to be penetrated, a penetrable seal of the reservoir, fluidly connecting, when coupled, the reservoir and the compartments of the cartridge through the penetrating element.

A penetrable seal reduces or prevents spilling and/or contamination of the liquid and/or the compartment. The seal may be elastic which enables that the seal closes again when decoupling the cartridge and the transfer device. The seal may be at least part of a cap. The reservoir may be a blood vial, in particular a "vacuum-filled" blood vial. The penetrating elements facilitate use of such penetrable seals.

One or more penetrating elements of the transfer device may be configured to penetrate a penetrable seal of the reservoir, fluidly connecting, when coupled, the reservoir and a gas supply and/or an outside atmosphere for gas transfer into the reservoir.

This facilitates emptying the reservoir, at least in part, by preventing an underpressure or overpressure in the reservoir. This may be particularly relevant for (gas-tight) sealed reservoirs such as a blood vial, in particular a "vacuum-filled" blood vial. It is preferred that the penetrating element be a hollow device, e.g. a hollow needle connected to a gas conduit through the transfer device, wherein an opening to the outside atmosphere may be provided with a gas permeable filter that is liquid impermeable to prevent spilling of liquid and/or contamination of the liquid.

The penetrating elements of the transfer device each may have a penetrating end being recessed in the transfer device, in particular being inaccessible for an average human adult finger.

This protects an operator from accidental harm.

The system may comprise a priming holder having a normal operating configuration, e.g. being positionable on a horizontal surface. The priming holder and the cartridge may have mated keying portions defining a relative position and orientation of the cartridge and the priming holder when coupled together by the mated keying portions. When the keying portions are mated and with the priming holder being in the normal operating configuration, the cartridge is held in a priming configuration. In the priming configuration the outlet of at least one compartment of the cartridge may have an opening to the compartment offset from a bottom wall defining a volume portion below the opening for receiving and holding an amount of liquid. The volume portion may be the second volume portion of a compartment having a first and a second volume portion as set out above.

This facilitates preparing the cartridge for use, in particular by filling one or more compartments of the cartridge with a reactant dose with which the liquid is to interact. The cartridge may be a small device, e.g., having about the size of a tube or vial as commonly used in medical laboratories. The cartridge itself may not have a very stable position on a work top, the priming holder may provide a stable stand. This may facilitate filling part of the compartment with a priming liquid flown along a side wall of the compartment and ensuring that the priming liquid does not accidentally contact and possibly contaminate and/or clog up the outlet and/or a filter in the outlet.

At least the cartridge and the transfer device, possibly also a priming holder and/or further similar cartridges may be sterile packaged in a single package. The cartridge and/or the transfer device may be formed disposable for one-time use.

In accordance with the preceding, a cartridge for the system may comprise at least one compartment having a compartment cavity configured to contain an amount of liquid and having an inlet and an outlet. In particular, the cartridge may comprise plural juxtaposed separate compartments each having a compartment cavity configured to contain a respective amount of liquid and having an inlet and an outlet, each inlet being a liquid inlet closed by a penetrable seal and each outlet being a gas outlet closed by a filter allowing passage of a gas but blocking liquid passage.

In line with the above, a method of handling a liquid, e.g., transporting, sampling and/or dividing a fluid, in particular a bodily fluid, more in particular blood, is provided. The method comprises providing a reservoir filled with the bodily fluid and providing a system as described herein and coupling the cartridge and the transfer device coupled by the mated keying portions, arranging the penetrating elements for penetrating the seal which may comprise penetrating the seal or a sealing element thereof. The method further comprises coupling the reservoir and the transfer device to each other and fluidly connecting the reservoir and the compartments of the cartridge through the transfer device. The method further comprises transferring at least a portion of the bodily fluid from the reservoir to the compartments.

The step of transferring at least a portion of the bodily fluid from the reservoir to the compartments may comprise providing a pressure difference across the respective filter to induce the transfer of at least a portion of the bodily fluid from the reservoir to the compartments, e.g. providing suction to an outlet of the compartments, the suction being through the respective filter, or by providing a pressure via an air inlet connecting the reservoir to ambient air.

In the method, the one or more compartments may be provided with a reactant dose and the method may further comprise letting the fluid interact with the reactant dose. The reactant may be a binding moiety and/or an antigen.

BRIEF DESCRIPTION OF THE DRAWINGS

The above-described aspects will hereafter be more explained with further details and benefits with reference to the drawings showing a number of embodiments by way of example.

FIG. 3, partly broken away;

FIG. 8A-8B are exploded views of the cartridge;

FIG. 9 is a front view of the cartridge;

FIGS. 9A-9C are cross section views, as indicated in FIG. 9;

FIG. 10 is partial cross section view of the cartridge in an optional priming holder, and FIGS. 11-17 indicate steps of a method of using the sample system;

FIGS. 20A and 2CB are cross sections of FIG. 19 at planes XXA and XXB, respectively, as indicated in FIG. 19;

FIGS. 30-32 show, respectively, a priming holder, an incubation holder and an analysis holder.

DETAILED DESCRIPTION OF EMBODIMENTS

It is noted that the drawings are schematic, not necessarily to scale and that details that are not required for understanding the present invention may have been omitted. Further, elements that are at least substantially identical or that perform an at least substantially identical function are denoted by the same numeral, where helpful individualised with alphabetic suffixes.

Figure 3:
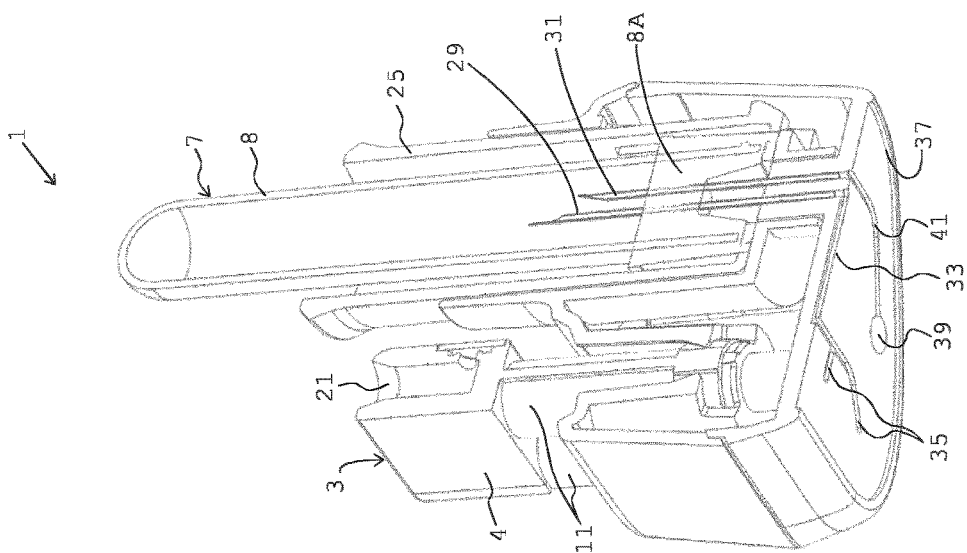
FIG. 3 is a cross section view of the sample system of FIG. 2, partly broken away.
Figure 2:
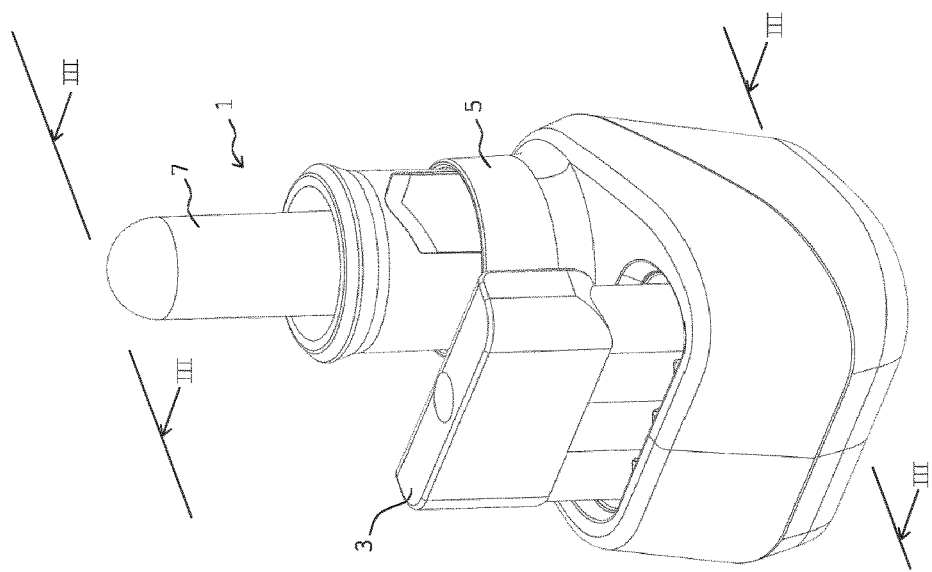
FIGS. 1 and 2 show an embodiment of a sample system.
Figure 1:
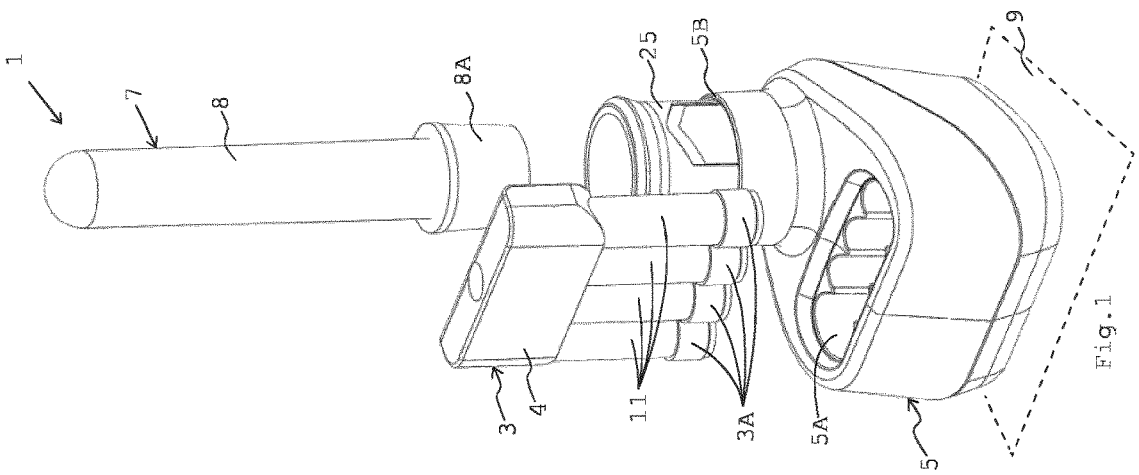

FIGS. 1-3 show a sample system 1 comprising a cartridge 3 (see also FIGS. 6-10) and a transfer device 5 (see also FIGS. 4-5) couplable to a liquid reservoir 7 as shown. The shown reservoir 7 is a standard blood vial 8 with a cap 8A but other reservoirs may be provided. The transfer device 5 is positionable on a horizontal surface, e.g. a table 9 as indicated, then having a normal operating configuration.

The cartridge 3 and the transfer device 5 have mated decouplable keying portions 3A, 5A, respectively, here formed such that the cartridge 3 can be inserted into the transfer device 5 and thereafter can be removed from it. The keying portions 3A, 5A define a relative position and orientation of the cartridge 3 and the transfer device 5 when coupled together by the mated keying portions. The keying portions 3A, 5A may be formed to allow coupling only in one relative position and orientation of the cartridge 3 and the transfer device 5 and to prevent coupling otherwise. In the normal operating configuration of the transfer device 5 a normal operating configuration of the sample system 1 is provided, here wherein both the cartridge 3 and the reservoir 7 are oriented vertical.

Similarly, the reservoir 7 and the transfer device 5 have decouplable keying portions, here formed by the cap 8A and a coupling portion 5B, such that the reservoir 7 can be inserted into the transfer device 5 defining a relative position and orientation of the two when coupled together.

As visible in FIGS. 7A-10 and discussed in more detail below, the cartridge 3 comprises a housing 4 defining plural separate compartments 11 each having a compartment cavity 13 configured to contain a respective amount of liquid. Each compartment 11 has a liquid inlet 15 and a liquid outlet 17 to the compartment cavity 13. The liquid inlet 15 is, in use, closed by a penetrable elastic seal 19, e.g. an elastic cap 19. Each outlet 17 is a gas outlet exits into space 20 holding a filter 22A (see FIG. 8B). The filter 22A is made of a filter material allowing passage of a gas through it but blocking liquid passage through it. The space 20 is sealed by a cap 22 in such a way that an open space remains between the filter 22A and the cap 22. The outlets 17 of each compartment 11 are fluidly connected via the space 20. An opening 21A is also fluidly connected to the space 20 forming the entrance of a channel leading to an exit 21 of the cartridge 3. The filter 22A is attached to the cartridge 3, e.g., by heat seals, so all gas leaving the outlets 17 as well as all gas entering the opening 21A is forced to pass the filter 22A. Gas passing the outlets 17 passes the filter 22A and flows via the open space between the filter 22A and the cap 22 and again via the filter 22A into the opening 21A to the exit 21. In another embodiment, the filter may be interrupted at the opening 21A so the gas needs to pass the filter 22A only once. The space 20 and the cap 22 thus form a manifold leading from each of the outlets 17 to the exit 21.

Figure 5:
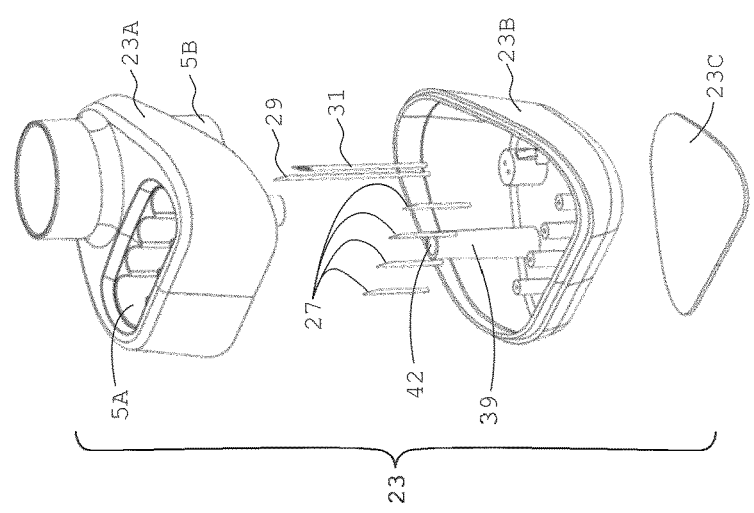
Figure 4:
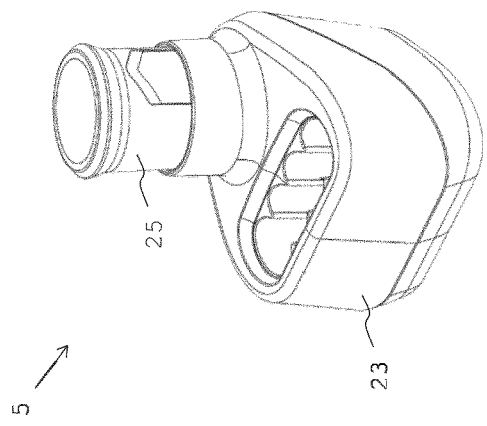
Figure 8A:
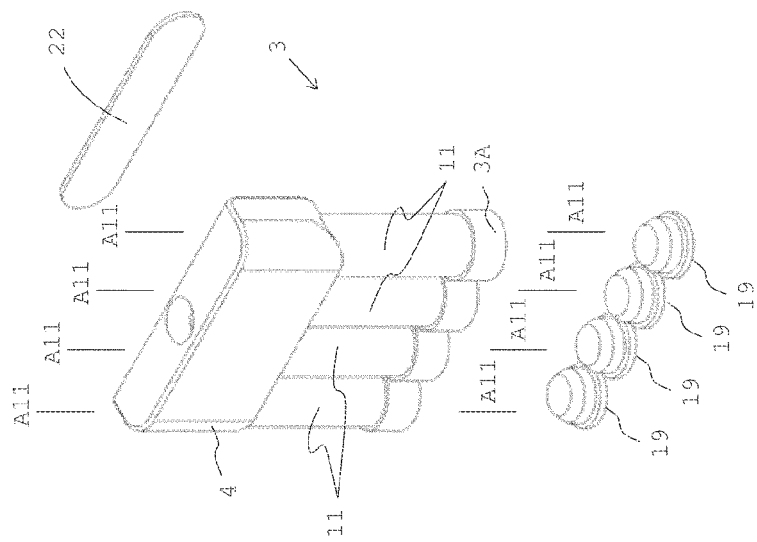
Figure 7B:
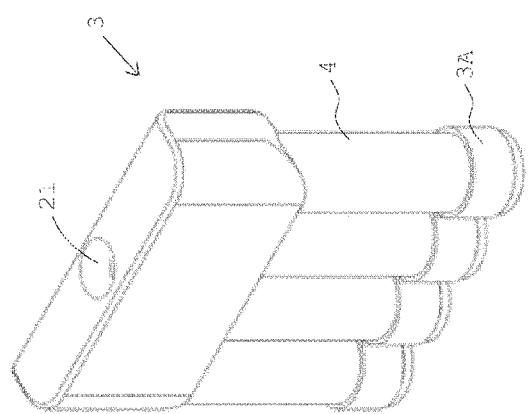
FIGS. 7A-7B are front and back perspective views of a cartridge for the sample system.
Figure 7A:
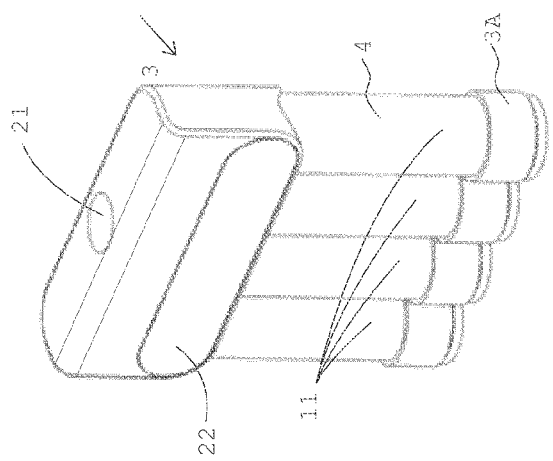

As visible in FIGS. 4-5, the shown transfer device 5 comprises a housing 23, here in the form of a base 23B, a cover 23A and a bottom plate 23C. Here, the cover 23A provides the keying portions 5A, 5B. The shown device 5 is provided with a reservoir adapter 25 in the coupling portion 5B mated to the selected reservoir 7; for other reservoir types and/or reservoir sizes appropriate reservoir adapters 25 may be provided, possibly in a set together with the housing 23. However, the transfer device 5 may be formed differently, e.g. mated to one type and size of reservoir, the transfer device 5 may also be monolithic.

The transfer device 5 comprises penetrating elements, here in the form of hollow needles 27, for penetration of the penetrable elastic seals 19 of the cartridge 3. The shown transfer device 5 also comprises further penetrating elements in the form of hollow needles 29, 31, for penetration of a penetrable portion of a (possibly elastic) seal of the reservoir 7, in particular the cap 8A. In the transfer device 5, the needles 27, 29, each have a lumen in fluid connection with each other. For that, the transfer device 5 is provided with channels, here in part being defined by cavities 33, 35 in the base 23B and the bottom plate 23C, when the latter is attached to the base 23B; in FIG. 4 the bottom plate 23C is absent and a recess 37 is visible in which the bottom plate 23C fits for closing off the cavities 33, 35 to define the channels and thus providing a manifold between the reservoir 7 and the compartments 11.

The further needle 31 also has a lumen, connected to a filter portion 39 by a further channel, here partly defined like the other channels by a cavity 41 in the base 23B and the bottom plate 23C, when attached to the base 23B. The filter portion 39 is at least partly open and is provided with a filter material (not shown) allowing passage of a gas but blocking liquid passage, so that, when coupled, the reservoir 7 and an outside atmosphere are fluidly connected, for gas transfer into the reservoir through (the filter material in) the filter portion 39, the channel and (the lumen of) the needle 31. Here, the filter portion 39 has an opening 42 inside the transfer device housing 23 to protect the filter material.

The tips of the needles 27-31, forming penetrating ends of the needles, are recessed in the respective portions 5A, 5B (25), of the transfer device 5 such that they are inaccessible for an average human adult finger. The needles may be of the same material (e.g. a polymer material) or another material than other parts (23A, 23B, 23C) of the housing 23, e.g. metal needles in polymer housing parts or different types of polymer materials.

Referring now to FIGS. 7A-10, in the shown embodiment of the cartridge 3 each compartment 11 is generally identical and has a generally cylindrical shape along an axis A11, the axes of each compartment 11 being parallel.

The inlet 15 and the outlet 17 are substantially opposite each other seen along the axis A11. The outlets 17 of the compartments 11 have an opening to the compartment cavity 13 oriented perpendicular to the axis A11. The outlets 17 are provided with tubes 43 protruding into the compartment cavity 13 separate from the side walls 45 of the compartments 11 and extending from a top wall 47 of the compartments 11 by a distance H2. Thus, the opening of the outlet 17 is offset from the top wall 47 of the compartment 11, and the compartment cavity 13 comprises a first volume portion V1 below the opening (extending for a length H1) and a second volume portion V2 above the opening, between the tube 43 and the walls 45 of the compartment. Note that in the shown embodiment the caps 19 closing the inlets 15 extend into the cavity 13 of the compartment 11 for a distance H3. The tube 43 is provided with an optional rupturing tip 49 next to the opening of the outlet 17 for rupturing liquid bubbles formed in a liquid inside the cavity 13 of the compartment 11.

When coupled and in the normal operating configuration (cf. FIGS. 2-9), in each compartment 11 the outlet 17 is positioned above the respective inlet 15 and the needles 27 of the transfer device 5 penetrate the seals 19 of each compartment 11. Further, the needles 29, 31 of the transfer device 5 penetrate the seal of the reservoir 7. Thus, when coupled, the reservoir 7 and each compartment cavity 13 of the cartridge 3 are fluidly connected through the penetrating elements 27-29 and the associated channels.

In order to test a liquid in a compartment 13 of the cartridge 3, the compartment 13 may be primed, e.g. provided with a reactant dose, the reactant e.g. being a binding moiety and/or an antigen. A fluid reactant dose 51 may be applied from a syringe 54 or a pipette through the inlet opening 15 as indicated in FIG. 10. The inlet opening 15 may thereafter be sealed. It is also possible that a fluid reactant dose 51 is applied through a previously applied reclosable seal, e.g. an elastic cap 19. The reactant dose 51 may also be a solid. A fluid reactant dose may be left to dry and/or solidify prior to filling the compartment 11 with the test liquid. For priming (one or more compartments 13 of) the cartridge 3, the cartridge may be placed in, or coupled to, a priming holder 50.

FIGS. 11-17 indicate a method of use. In FIG. 11 a system 1 as described herein is provided; see also FIG. 1. The cartridge 3 preferably is empty but (at least some of its compartments 11) may be primed with a reactant dose. The reservoir 7 is provided with an amount of test liquid 53, e.g. a vial that is vacuum-filled with blood sample, as commonly used for human and animal blood testing.

In FIG. 12 the cartridge 3 is coupled to the transfer device 5. Preferably this is done prior to coupling of the reservoir 7 to the transfer device 5 to prevent leaking of test liquid 53 from the reservoir 7.

The cartridge coupling portion 5A and/or the reservoir coupling portion 5B of the transfer device 5 may be provided with a hygienic seal, e.g. a tape (not shown), that may be removed before coupling the cartridge 3 and/or, respectively, the reservoir 7. In some cases, the cartridge 3 and the transfer device 5 may be sold as a pre-coupled unit.

Figure 13:
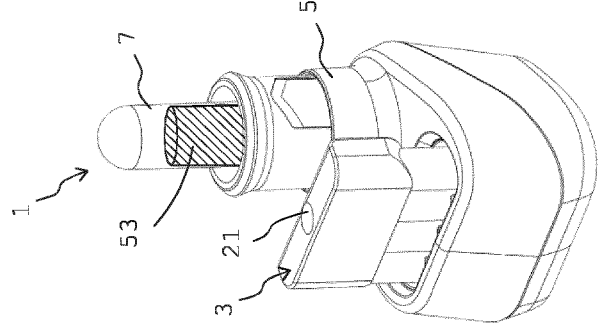

In FIG. 13, both the cartridge 3 and the reservoir 7 are coupled to the transfer device 5, see also FIGS. 2-3; the penetrating elements of the transfer device 5 penetrate the elastic seals of both the cartridge 3 and the reservoir 7, fluidly connecting the compartments 13 to the reservoir.

Figure 14:
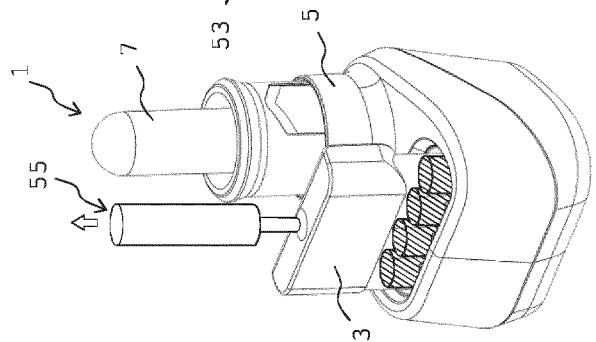

In FIG. 14, a suction device 55 (schematically shown) is connected to the exit 21 of the cartridge 3. The suction device 55 may be a syringe, a pipette-pump, a connection to a hospital vacuum line or any other suitable apparatus. By action of the suction device 55, gas is drawn from the cavities 13 of the cartridge so that the test liquid is drawn into the cavities 13 from the reservoir 7 through the fluid connection established by the transfer device 5 (cf. FIGS. 2-6 and associated discussion).

In the compartments 13, the liquid will be drawn up until the liquid wets the filter and further transfer is prevented. Thus, all compartments 13 are filled to their desired level, irrespective of the filling speed and/or volume of other containers 13 of the cartridge 3. In the compartments 13, the volume V2 are left open. Accidental bubbles in the liquid will be ruptured by the respective rupturing tips 49.

The needle 31 and the associated filter in filtering portion 39 enable gas inflow into the reservoir to replace liquid 53 removed from the reservoir 7 and preventing underpressure. In the shown embodiment the tip of needle 29 is higher than the tip of the needle 31. This has the advantage that needle 29 penetrates the seal first and releases the underpressure. Alternatively, the tip of the needle 31 for gas inflow may extend further into the reservoir (i.e. be located higher) than the tip of the needle 29 for liquid outflow, so as to prevent drawing gas bubbles from needle 31 into needle 29 and into the cartridge 3. If both needles 29, 31 are of equal length, this bubble drawing can be prevented by means of a partition between the two lumina.

Figure 15:
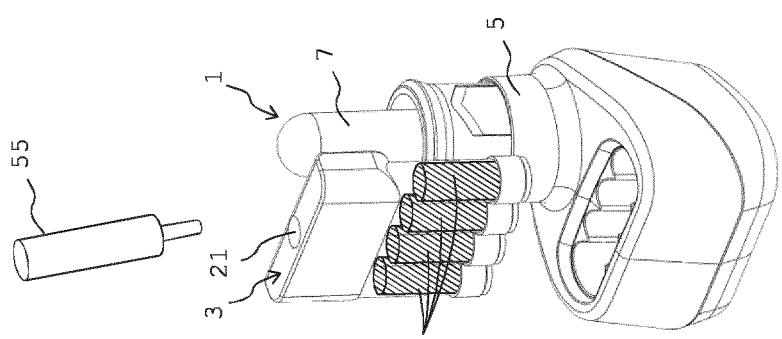

After the cartridge 3 is sufficiently filled, the suction device 55 and the cartridge 3 can be removed (FIG. 15). The suction device 55 having not been in contact with the liquid can be re-used. In case the cartridge 3 is at least partly translucent or even transparent, the filling levels of the respective compartments 11 may be visually assessed. The cartridge 3 can then be used for transporting the liquid and/or for further steps of a test protocol on the liquid. This may comprise temperature and/or light conditioning of the liquid.

Figure 17:
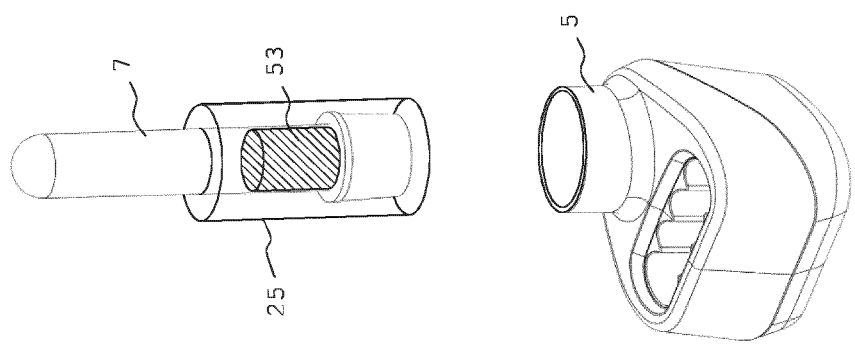
Figure 16:
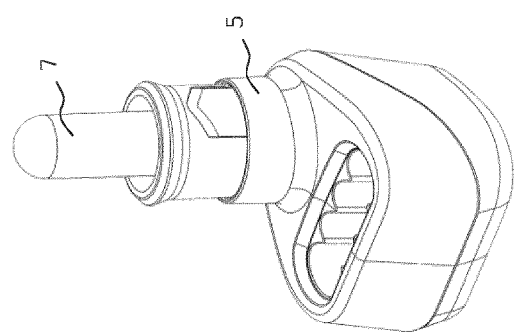

When the reservoir 7 is at an underpressure compared to the environmental pressure, after removal of the cartridge, liquid may be drawn back into the reservoir 7 from (the channels in) the transfer device 3. In particular in case of biological liquids e.g. blood, this may reduce contamination risks. The transfer device 5 and the reservoir 7 may be safely discarded after use (FIG. 16) or the reservoir may be decoupled from the transfer device 5, possibly together with the reservoir adapter 25, for separate disposal and/or further use of possibly remaining liquid 53 (FIG. 17).

FIGS. 18-29 shows various views of (details of) a further embodiment; a sample system 100 (FIGS. 18-20B) comprising a cartridge 103 and a transfer device 105 couplable to a liquid reservoir 7. The transfer device 105 is shown in particular in FIGS. 21-23. The cartridge 103 is shown in particular in FIGS. 24-29.

This embodiment is largely similar to the systems explained before, to avoid repetition in the following mainly differences are discussed.

In this case, the cartridge 103 is provided with an optional lateral protrusion providing a cap holder 157 (see below). The transfer device 105 comprises a receptacle 159 for the cartridge 103, at least part of which being shaped in accordance with the cartridge 103 to provide mated decouplable keying portions 157-159.

Figure 6:
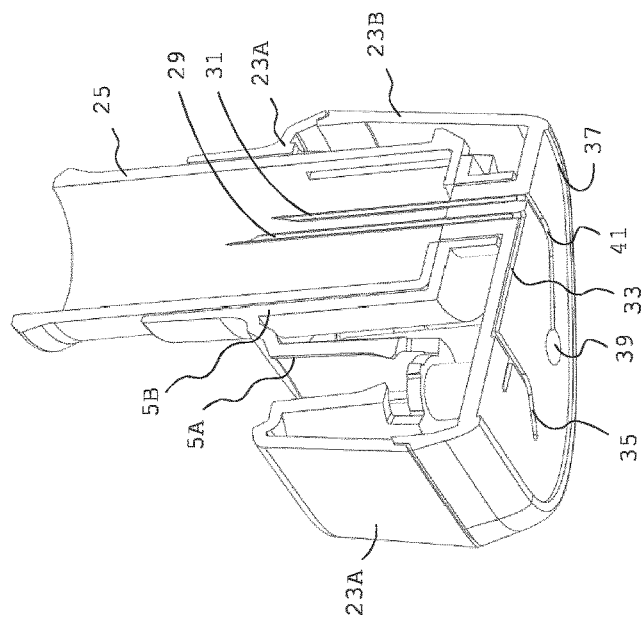
FIGS. 4-6 show the transfer device of the sample system of FIGS. 1-3 in exploded view and in cross section view cf.

Best visible in FIGS. 20A-23, this embodiment of the transfer device 105 again comprises a housing 123, in turn comprising a base 123B, a cover 123A a bottom plate 123C together defining channels by (closing) cavities 133, 135, 141 (cf. FIGS. 5-6). The transfer device 105 comprises hollow penetrating elements 127, which in this case do not have needles as in previously discussed embodiments. The present penetrating elements 127, in particular at least part thereof, are mated to inlets 115 of the cartridge 103 (see below) to provide an at least liquid-tight, preferably also at least substantially gas-tight connection between the two (127, 115). E.g., the elements 127 and the inlets 115 may at least partly be provided with standard Luer-tapers and/or other standardised connections and/or proprietary connections. The tips of the elements 127 may be recessed in the transfer device 105 such that they are inaccessible for an average human adult finger, however, Luer tapers tend to be safe to the touch to at least an average human adult finger. The elements 127 may be of the same material or of another material than other parts of the housing 123 of the transfer device 105, e.g. metallic and/or polymer materials.

Likewise, instead of hollow needles 29, 31, the transfer device 105 comprises a penetrating element 130 for penetration of a penetrable portion of a (possibly elastic) seal of (a cap 8A of) the reservoir 7. This penetrating element 130 comprises plural lumina 130A, 130B, in fluid connection with (lumina of) the elements 127 and, respectively, a filter portion 139, via the channels in the housing 123.

Best seen in FIGS. 20B, 25-29, the cartridge 103 comprises a compartment portion 164 and a manifold portion 166. The compartment portion 164 defines plural separate compartments 111 each having a compartment cavity 113 configured to contain a respective amount of liquid. In the shown embodiment, the compartment portion 164 and the manifold portion 166 are separable, the latter providing a cap to the former.

Each compartment 111 has a liquid inlet 115 and an outlet 117 to the compartment cavity 113. As an option, the liquid inlet 115 is provided with a small-sized opening 119 to provide a capillary seal, however a septum or other seal may also be provided. One or more liquid inlets 115 may at least partly be closed by one or more optional caps 119 which may be interconnected to a cap assembly 119A as shown. Here, cap(s) 119 may be provided to a user in the cap holder 157. The cap holder 157 may also be used to store or more caps temporarily and/or reversibly when removed from inlet(s) 115.

As shown, the shown manifold portion 166 is configured for coupling with the compartment portion 164 and in coupled configuration close off the compartments 111 with respective lids 168. In the coupled configuration the connection between the manifold portion 166 and the compartment portion 164 preferably is liquid tight or preferably even gas tight other than through the filter and through an exit 121 (see below), e.g. using an O-ring, an adhesive or similar or combinations of the foregoing. The lids 168 may provide the outlets 117 and they may protrude at least partly into the compartment 111 with a protruding portion 169. The protruding portions 169 may define a space between them and a wall of the compartment 113 adjacent to the latter, thus providing an optional volume V2. The protruding portions 169 may also form or be provided with a rupturing tip for rupturing undesired bubbles in the liquid.

Each outlet 117 is a gas outlet and exits into space 120 holding a filter 122A and from there to the exit 121 in a cap 122, optionally formed in the manifold portion 166 in such a way that an open space remains between the filter 122A and the exit 121 of the cap 122.

Instead or in addition, one or more of the outlets 117 may be provided independently with a filter 122B, such that the outlet is closed by the filter 122B, which enables filling the compartment to a level determined by the respective filter 122B.

The manifold portion 166 is provided with an optional shroud 170. The shroud 170 may cover, as shown, one or more sides of the compartment portion 164 partly or wholly and it may, as shown, extend around and/or clamp onto at least part of the compartment portion 164. The shroud 170 may serve one or more purposes such as supporting a cap holder 157, providing the compartment portion 164 with a shield against light and/or mechanical damage, providing a visual and/or tactile labelling surface, providing an engagement structure for human and/or automated manipulation, providing a stand, providing one or more keying portions to other parts of the system, securing one or more lids 119, 168 on respective compartment(s); a shroud may be provided with a machine-readable non-optic tag e.g. an RFID-tag.

Figure 26:
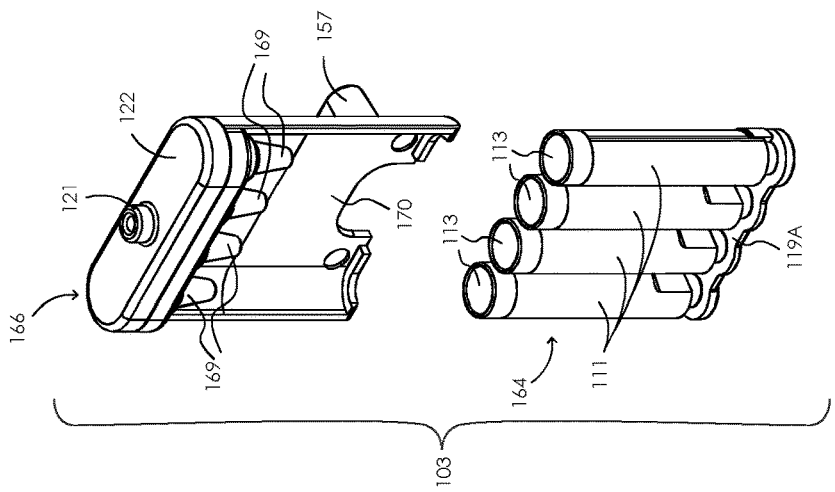
FIG. 26 is a partial exploded view of the cartridge of FIGS. 24-25, showing a compartment portion and a manifold portion.
Figure 25:
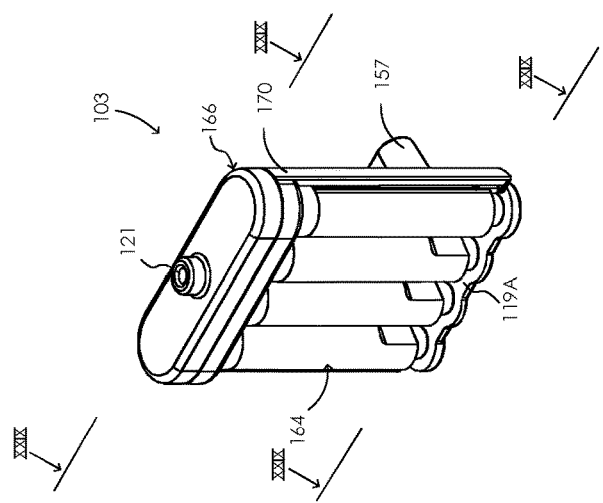
FIGS. 24-25 are front and rear perspective views of the cartridge of FIGS. 18-20B.
Figure 24:
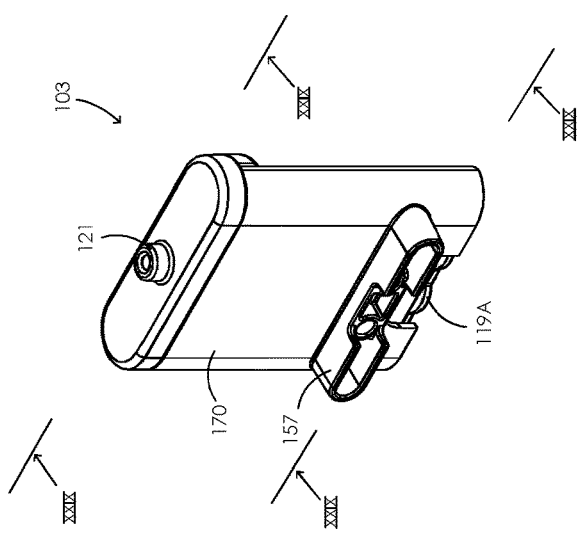
Figure 29:
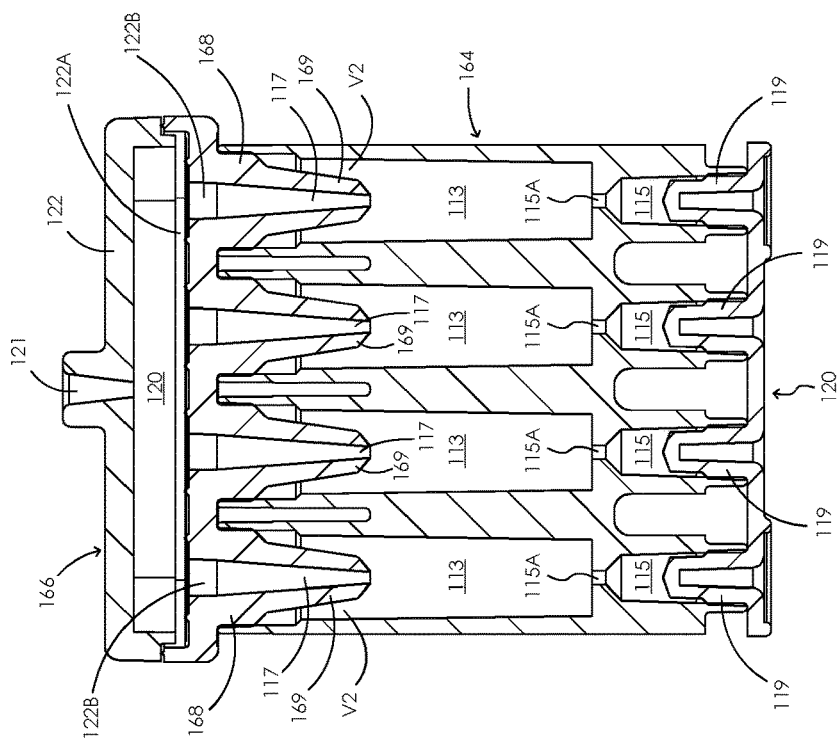
FIG. 29 is a cross section view of the cartridge of the cartridge of FIGS. 24-25 at plane XXIX.
Figure 28:
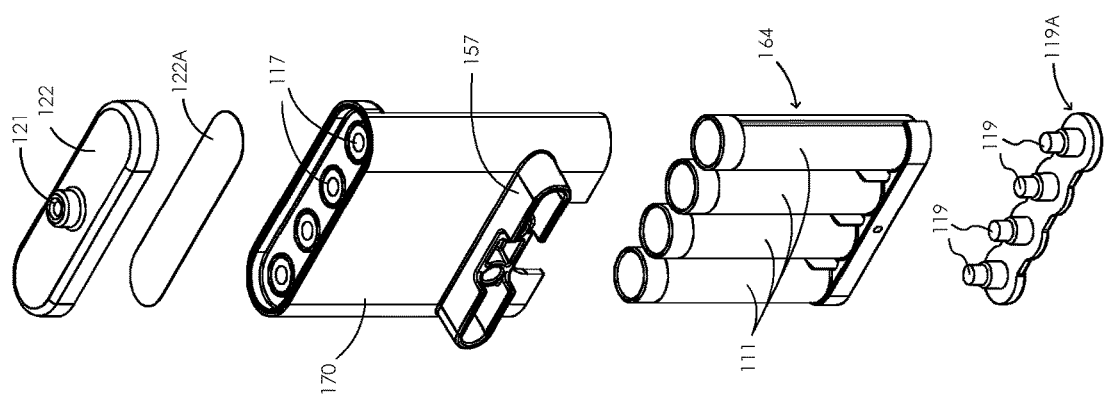
FIG. 28 is an exploded view of the cartridge of FIGS. 24-25.
Figure 27A:
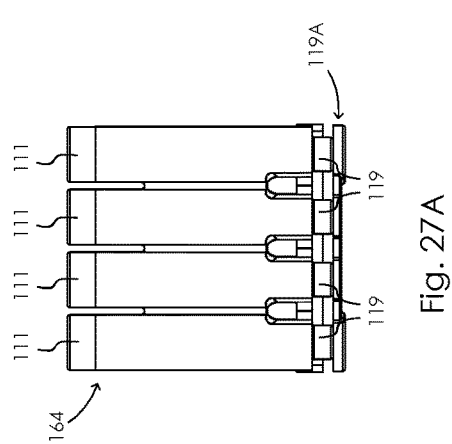
FIGS. 27A and 27B show the compartment portion of the cartridge of FIGS. 24-25 in front and perspective views, respectively.
Figure 27B:
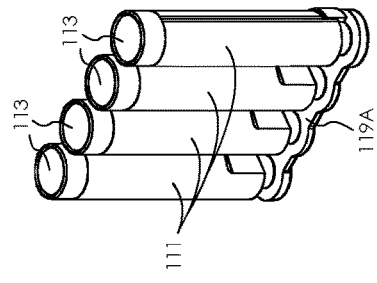

Best seen in FIGS. 26-27, the manifold portion 166 may be removed from the compartment portion 164, which may open one or more compartments 111, here providing an open end opposite the inlets 115.

Use of the embodiment is largely in accordance with FIGS. 10-17; this is summarised below with reference to FIGS. 18-29, wherein in particular FIGS. 18-21 show the system 100 in different stadia of use.

Figure 18:
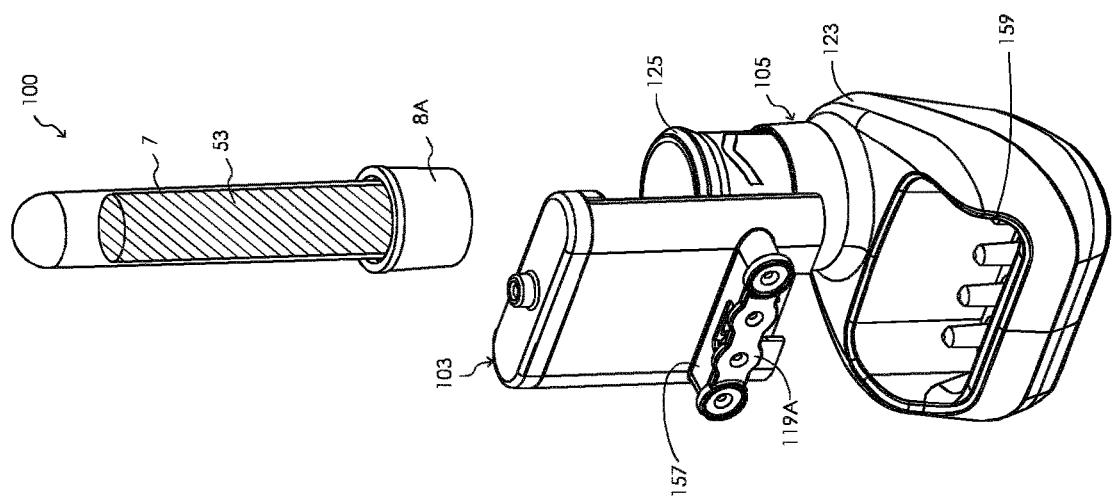

FIG. 18 shows the sample system 100 prior to testing (cf. FIG. 11). The reservoir 7 comprises an amount of liquid 53 to be tested, e.g. a blood sample.

Initially, the cartridge 103 may be empty. However, one or more of its compartments 111 may be primed with a reactant dose. For priming, the compartment portion 164 and manifold portion 166 may be decoupled, facilitating access to the cavities 113 of the compartments 111, see FIGS. 26-27. Also, the compartment portion 164 may be placed in a priming holder 150A for one or more containers 103, compare FIGS. 26-27 and FIG. 30 with FIG. 10. The priming holder 150A may be referred to as filling tray or priming tray. The priming holder 150A and the cartridge 103 may comprise matching keying portions 152B defining a relative position and orientation of one or more cartridges 103 and the priming holder 150A.

Figure 19:
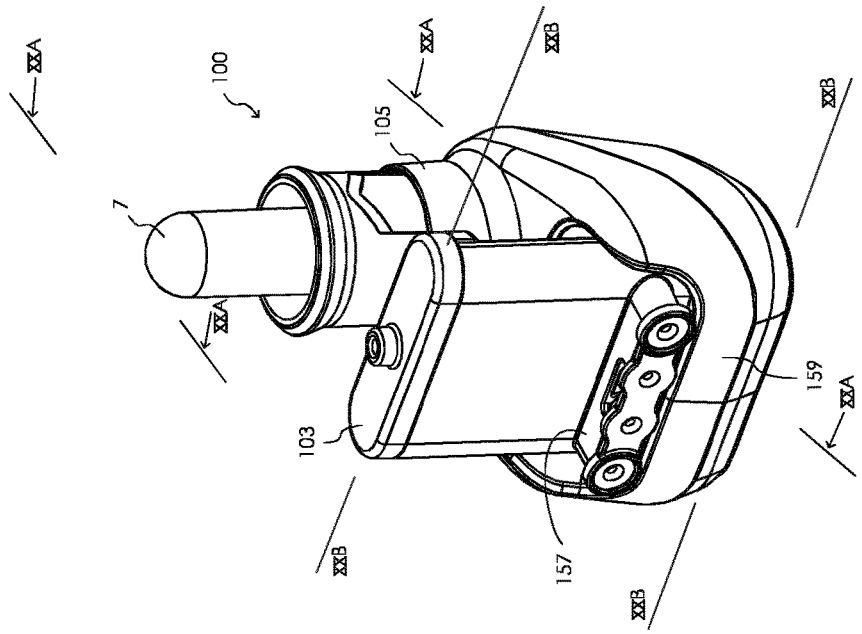
FIGS. 18-19 show another embodiment of a sample system.
Figure 20B:
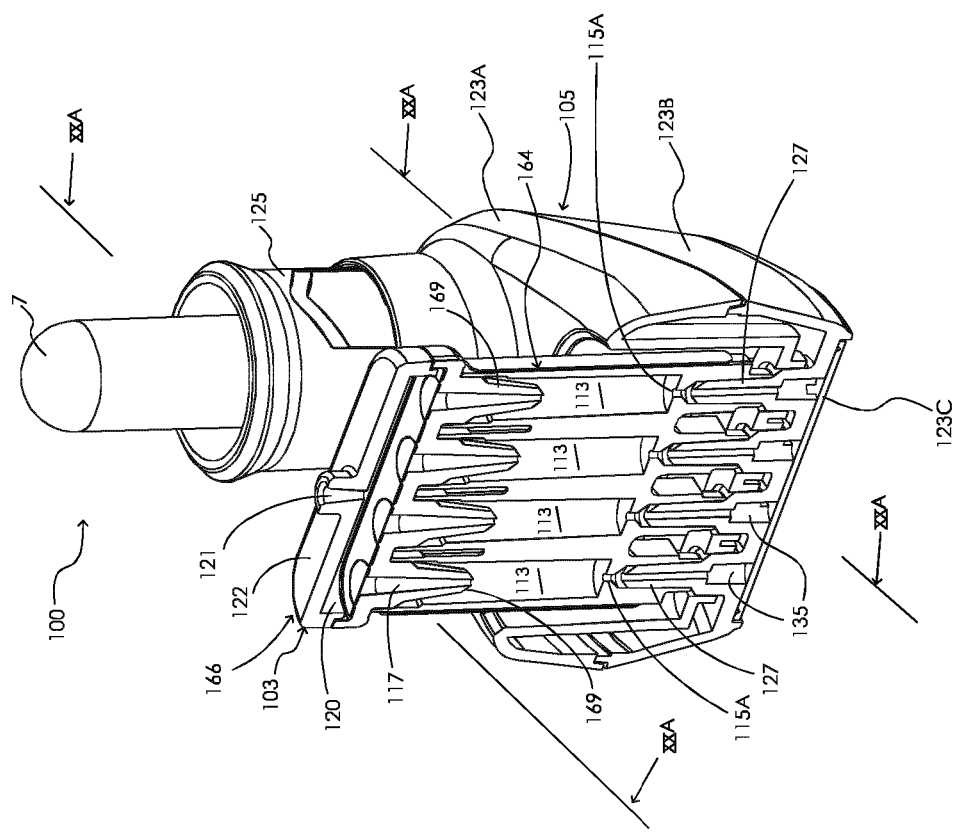
Figure 20A:
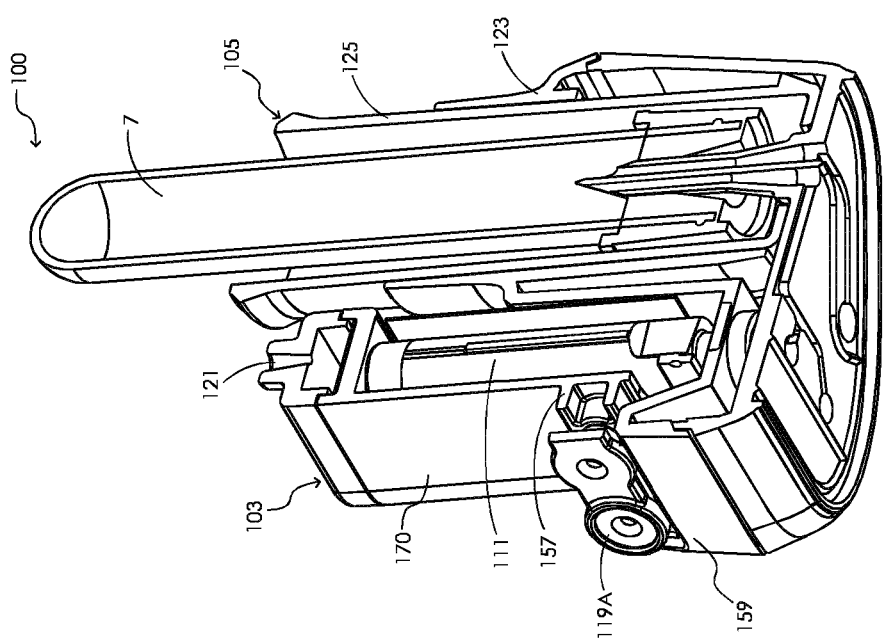
Figure 23:
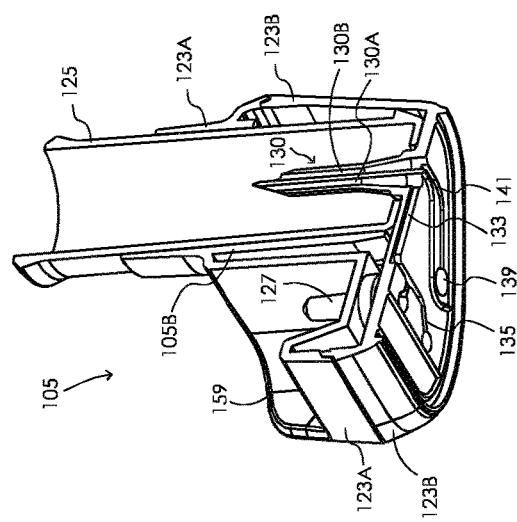
FIGS. 21 and 23 show a transfer device of the embodiment of FIGS. 18-20B in perspective and exploded view and in cross section view at the same plane, respectively.
Figure 22:
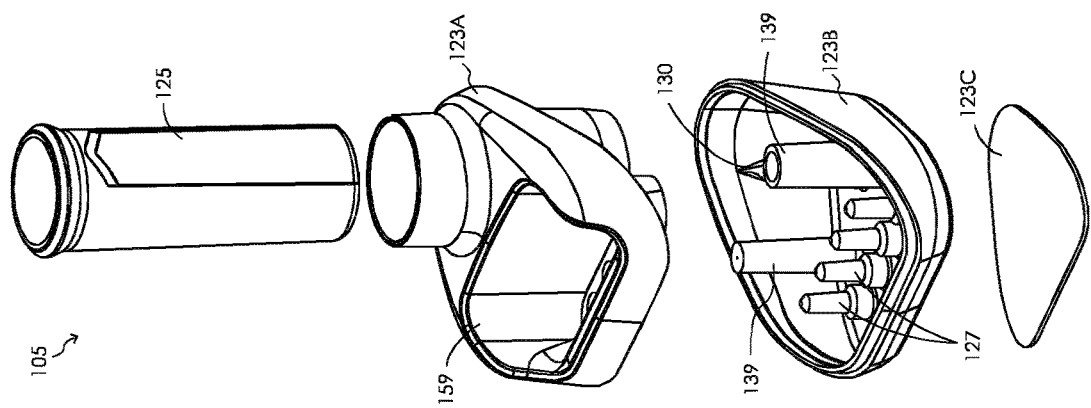
Figure 21:
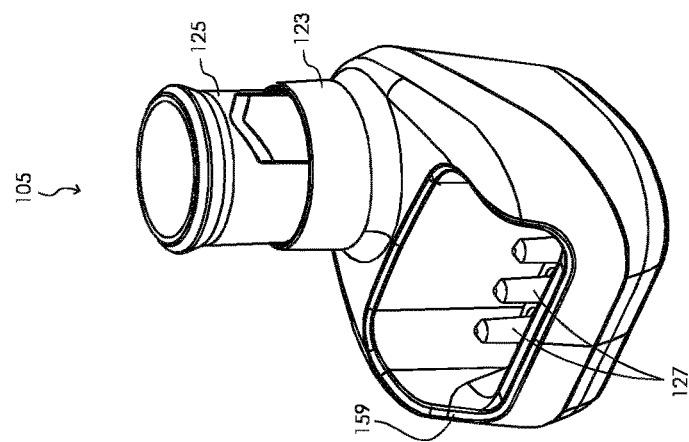

In FIGS. 19 and 20A-20B, both the cartridge 103 and the reservoir 7 are coupled to the transfer device 105 (cf. FIG. 13). When coupled, the penetrating elements 127, 130 of the transfer device 105 connect the cartridge 103 and the reservoir 7, fluidly connecting (the cavities 113 of) the compartments 111 to the reservoir 7.

Preferably, the cartridge 103 is coupled to the transfer device 105 prior to coupling of the reservoir 7 to the transfer device 5 to prevent leaking of test liquid 53 out of the reservoir 7 and from (e.g. the elements 127 of) the transfer device 105 (cf. FIG. 12).

Next, a suction device (not shown) is connected to the exit 121 of the cartridge 103 (cf. FIG. 14). As described above, by action of the suction device, gas is drawn from the compartments 111 of the cartridge 103 through the filter 122A so that the test liquid is drawn into the cavities 113 from the reservoir 7 through the fluid connection established by the transfer device 105 until the liquid wets the filter 122A and further transfer is prevented. Volumes V2 may be left open and accidental bubbles in the liquid in the compartments 111 may be sucked out of the liquid and/or be ruptured by the respective rupturing tips.

After the compartments of the cartridge 103 are sufficiently filled, the suction device can be removed and the cartridge 103 can be removed from the transfer device. The cartridge 103 can then be used for transporting the liquid and/or for further steps of a test protocol on the liquid (see below). The transfer device 105 and the reservoir 7 may, as before, be decoupled and independently used again, used further, and/or be safely discarded after use (cf. FIGS. 15-17).

After filling and for one or more of incubation, testing and transportation, one or more inlets 115 of the container 103 may be covered and/or closed off with caps 119, permanently or temporarily (FIGS. 24-29). Thus, the inlet 115 and/or a seal thereof, in particular a capillary seal, may be protected. A cap 119 may be inserted into an inlet 115, but a cap gripping over compartment walls may also be provided. One or more caps 119 may form a stand for the cartridge. One or more of the caps 119 or the cap assembly 119A and the cartridge may comprise keying features for defining a desired relative orientation of the cap 119 and/or cap assembly 119A and respective container inlets 115. In the shown embodiment, caps 119 may be stored in (the cap holder 157 of) the cartridge 103 also when not in use. In the cap holder 157, the caps 119 may have been stored sterile, or at least clean and/or safe from endotoxins. In such case the cap holder 157 may be closed off with a cap or a sealing film and/or in another suitable manner (not shown). As an option, in particular after removal of one or more caps 119 from the cap holder 157, at least part of the cap holder 157 may be removed temporarily or permanently from (the shroud 170 of) the cartridge 103, e.g. to reduce bulk of the cartridge 103 in further procedures and/or to indicate that the cartridge 103 is in use or has been used. As an option, at least part of one or more of the caps 119 may be attached to the cartridge to prevent dropping and/or loss; e.g. using a hinge, a film or a filament connection.

For incubation and/or transportation, the cartridge 103 may be placed in an incubation holder 150B, which may also be referred to as incubation tray, see FIG. 31. The incubation holder 150B may comprise connection portions 152B for securely holding one or more cartridges 103 and/or the incubation holder 150B and the cartridge 103 may comprise matching keying portions defining a relative position and orientation of the cartridge 103 and the incubation holder 150B.

For testing contents of cavities 113 of one or more compartments 111, the respective compartments 111 may be opened to gain access to the contents. In the shown embodiment all compartments 113 may be opened together by removing the manifold portion 166 from the compartment portion 164 (FIGS. 26-27). However, access though a seal is also conceivable.

The compartment portion 164 may fit a carrier for carrying plural compartment portions, e.g. an analysis holder (or: "analysis tray") 150C. The carrier may be couplable to an assay- and/or pipetting apparatus. The compartment portion 164 and such carrier 150C may comprise matching keying portions 152C for defining a relative position and orientation of (the compartment portion 164 of) the cartridge 103 and the carrier when mated, possibly in a releasable manner. Note that the optional keying portions of two or more of the transfer device 105, a priming holder, an incubation holder, an analysis holder and/or another carrier may all match one or more keying portion(s) of (the compartment portion 164 of) the cartridge 103 so that a clear rapport may be established between a position and/or orientation of the (the compartments 111 of) the cartridge 103 in each respective step of a method of use. This may prevent errors and/or at least facilitate detection thereof; e.g. different compartments may be of have been provided with different priming reactant doses in a predetermined sequence or pattern for plural simultaneous tests and/or controls.

The disclosure is not restricted to the above described embodiments which can be varied in a number of ways within the scope of the claims. For instance, one transfer device 5 may be couplable to plural cartridges 3 simultaneously with respective mated decouplable keying portions, fluidly connecting, when coupled, the reservoir and each compartment cavity of each coupled cartridge.

Further, one or more portions of the cartridge and/or transfer device may be provided with different materials and/or material finishes for different functions. E.g. a smooth and/or polished portion may facilitate operation with a vacuum suction tool; a rough portion may facilitate operation by human and/or automated gripping, and an elastic portion may facilitate clamping and/or sealing a connection between portions. E.g., for the latter, one or more of penetrating elements 127 and inlets 150 may be lined with an elastic layer. Overmoulding at least part of the transfer device and/or cartridge may facilitate manipulation as an integrated whole and increase robustness of the respective part.

It is also possible that one transfer device 5 is couplable to plural reservoirs 7, e.g., simultaneously or sequentially, with respective decouplable keying portions, fluidly connecting, when coupled, each reservoir 7 and each compartment cavity of each coupled cartridge.

The (functionality of the) needles 29, 31 may be combined in a single needle having two lumina, each fluidly connected to an appropriate channel.

In the cartridge more or less compartments may be provided and any number of compartments may be arranged differently, although an array form or a row form as shown in the Figures may be preferred.

Elements and aspects discussed for or in relation with a particular embodiment may be suitably combined with elements and aspects of other embodiments, unless explicitly stated otherwise.

The invention claimed is:

1. A liquid handling system comprising a cartridge, and a transfer device couplable to a liquid reservoir,
wherein the cartridge comprises plural compartments each having a compartment cavity configured to contain an amount of liquid and having an inlet and an outlet, each inlet being closed by a penetrable seal and each outlet being closed by a filter allowing passage of a gas but blocking liquid passage,
wherein a level of each compartment is determined by the respective filter,
wherein the transfer device and the cartridge have matching first keying portions defining a relative position and orientation of the cartridge and the transfer device when the first keying portions are mated, and wherein one or more penetrating elements of the transfer device are arranged for penetrating, or causing to be penetrated, the seal of each compartment when the first keying portions are mated, for fluidly connecting, when coupled, the reservoir and each compartment cavity of the cartridge through the one or more penetrating elements.

2. The system according to claim 1, wherein each outlet of each compartment is fluidly connected to each other forming a manifold from each outlet of each compartment to an exit.

3. The system according to claim 1, wherein, when the cartridge and the transfer device are coupled by the mated first keying portions, the outlet of at least one of the plural compartments has an opening to the at least one of the plural compartments which is offset from a top wall of the at least one of the plural compartments, such that the compartment cavity of the at least one of the plural compartments comprises a first volume portion below the opening and a second volume portion above the opening.

4. The system according to claim 1, wherein at least one of the plural compartments contains a reactant dose to interact with at least a portion of the liquid.

5. The system according to claim 1, wherein at least one of the plural compartments comprises a rupturing tip for rupturing liquid bubbles formed in a liquid inside the compartment.

6. The system according to claim 1, wherein at least some of the compartment cavities have identical volumes and/or the outlets of the plural compartments are positioned at equal heights when the cartridge and the transfer device are coupled and in a normal operating configuration.

7. The system according to claim 1, wherein the transfer device and the reservoir have matching second keying portions defining a relative position and orientation of the reservoir and the transfer device when the second keying portions are mated.

8. The system according to claim 1, wherein one or more penetrating elements of the transfer device are configured to penetrate, or to cause to be penetrated a penetrable seal of the reservoir, fluidly connecting, when coupled, the reservoir and the plural compartments of the cartridge through the penetrating element.

9. The system according to claim 1, wherein one or more penetrating elements of the transfer device are configured to penetrate a penetrable seal of the reservoir, fluidly connecting, when coupled, the reservoir and a gas supply and/or an outside atmosphere for gas transfer into the reservoir.

10. The system according to claim 8, wherein the one or more penetrating elements of the transfer device each have a penetrating end, and the penetrating ends are recessed in the transfer device.

11. The system according to claim 3, comprising a priming holder having a normal operating configuration, wherein the priming holder and the cartridge have matching third keying portions defining a relative position and orientation of the cartridge and the priming holder, and wherein when the third keying portions are mated and the priming holder is in the normal operating configuration, the cartridge is held in a priming configuration in which the outlet of at least one of the plural compartments has an opening to the compartment offset from a bottom wall defining a volume portion below the opening for receiving and holding an amount of liquid,
wherein the volume portion is the second volume portion.

12. The system according to claim 7, wherein one or more penetrating elements of the transfer device are configured to penetrate, or to cause to be penetrated a penetrable seal of the reservoir, fluidly connecting, when coupled, the reservoir and the plural compartments of the cartridge through the penetrating element.

13. The system according to claim 2 wherein the exit is provided with a connector for connection to a suction device.

14. A cartridge for a liquid handling having a transfer device with one or more penetrating elements the cartridge comprising plural compartments each having a compartment cavity configured to contain an amount of liquid and having an inlet and an outlet, each inlet being closed by a penetrable seal and each outlet being closed by a filter material allowing passage of a gas but blocking liquid passage, wherein a filling level of each compartment is determined by the respective filter, and wherein the cartridge has first keying portions defining a relative position and orientation of the cartridge to the transfer device, when the first keying portions are mated with corresponding transfer device keying portions such that the one or more penetrating elements of the transfer device penetrate, or cause to be penetrated, a seal of each compartment.

15. The cartridge according to claim 14, wherein each outlet of each compartment is fluidly connected to each other forming a manifold from each outlet of each compartment to an exit.

16. A method of handling a fluid, comprising providing a reservoir filled with the fluid;
providing a system comprising a cartridge, and a transfer device couplable to the reservoir, the cartridge comprising plural compartments, each compartment having a compartment cavity configured to contain an amount of liquid and having an inlet and an outlet, each inlet being closed or closable by a penetrable seal and each outlet being closed by a filter material allowing passage of a gas but blocking liquid passage, wherein a filling level of each compartment is determined pined by the respective filter, and wherein the transfer device and the cartridge have matching first keying portions defining a relative position and orientation of the cartridge and the transfer device when the first keying portions are mated, and wherein one or more penetrating elements of the transfer device are arrangeable for penetrating the seal of each compartment;
coupling the cartridge and the transfer device by the first keying portions;
arranging the penetrating elements for penetrating the seal;
coupling the reservoir and the transfer device of the system;
fluidly connecting the reservoir and the plural compartments of the cartridge through the transfer device; and
transferring at least a portion of the fluid from the reservoir to the plural compartments.

17. The method according to claim 16,
wherein transferring at least a portion of the fluid from the reservoir to the compartments comprises providing a pressure difference across the respective filter to induce the transfer of at least a portion of the fluid from the reservoir to the compartments.

18. The method according to claim 16,
wherein at least one compartment is provided with a reactant dose, and the method further comprises letting the fluid interact with the reactant dose.

19. The method according to claim 17, wherein at least one compartment is provided with a reactant dose, and the method further comprises letting the fluid interact with the reactant dose.

20. The method according to claim 17 and providing suction to an outlet of at least one of the compartments, the suction being through the respective filter.

* * * * *